United States Patent [19]

Totten et al.

[11] 4,339,581
[45] Jul. 13, 1982

[54] MILDEWCIDAL SILANE COMPOUNDS

[75] Inventors: George E. Totten, West Haverstraw; John P. Wesson, Croton-on-Hudson, both of N.Y.; Thomas C. Williams, Ridgefield, Conn.; Robert G. Eagar, Jr., Yorktown Heights, N.Y.

[73] Assignee: Union Carbide Corporation, Danbury, Conn.

[21] Appl. No.: 192,604

[22] Filed: Sep. 30, 1980

[51] Int. Cl.$^3$ .................. A01N 55/00; C07F 7/18
[52] U.S. Cl. .................. 546/14; 424/184; 556/418; 556/420; 556/427
[58] Field of Search .................. 546/14; 556/418, 420, 556/427; 424/184

[56] References Cited

U.S. PATENT DOCUMENTS

| | | | |
|---|---|---|---|
| 3,253,009 | 5/1966 | Allen et al. | 260/448.8 |
| 3,542,786 | 11/1970 | Weesner et a. | 260/279 |
| 3,627,806 | 12/1971 | Le Grow | 556/427 |
| 3,673,233 | 6/1972 | Golitz et al. | 556/420 |
| 3,692,798 | 9/1972 | Barcza | 260/309 |
| 3,719,679 | 3/1973 | Michael et al. | 260/448.2 N |
| 3,794,736 | 2/1974 | Abbott et al. | 424/184 X |
| 3,860,709 | 1/1975 | Abbott et al. | 424/184 |

FOREIGN PATENT DOCUMENTS

| | | |
|---|---|---|
| 1010782 | 5/1977 | Canada. |
| 1806758 | 7/1970 | Fed. Rep. of Germany. |
| 2632417 | 2/1977 | Fed. Rep. of Germany. |
| 1386876 | 3/1975 | United Kingdom. |

OTHER PUBLICATIONS

Lutz et al., Organic Coatings and Plastic Chemistry, vol. 38 (1976), pp. 195-201.
Pittman, J. Coating Technology, vol. 48 (1976), pp. 31-37.

*Primary Examiner*—Richard Raymond
*Attorney, Agent, or Firm*—Paul W. Leuzzi, II

[57] ABSTRACT

Novel mildewcidal compounds of the formula $(RO)_3Si(CH_2)_3XOAr$ wherein R is lower alkyl, X is —NHC(O)— or —S(CH$_2$)$_2$C(O)—, and Ar is aryl, and their use in latex paints.

11 Claims, No Drawings

MILDEWCIDAL SILANE COMPOUNDS

CROSS REFERENCE TO RELATED APPLICATION

Ser. No. 192,603 filed on even date herewith, discloses pentachlorophenyl 3-(triethoxysilyl)propyl ether and its use as a mildewcidal agent in latex paints.

BACKGROUND OF THE INVENTION

1. Field of the Invention

This invention relates to a small class of novel trialkoxysilicon compounds which has been found to exhibit mildewcidal activity and to latex paints containing such mildewcidal compounds.

2. Description of the Prior Art

Mildewcidal-induced defacement of paint film and other organic coatings is a serious problem faced by the coatings industry, resulting in several tens of million of dollars of damage annually. Mildew growth destroys coating integrity by a series of microbial (including bacterial and fungal) degradations of paint film components. Hydroxyethyl cellulose, which is often used as a binder in water-based latex paint formulations, is especially susceptible to microbial degradation, and therefore latex paints as a class are especially susceptible to mildew attack.

Although the exact mechanism of mildew growth on a paint film has not yet been determined, considerable evidence suggests that mildew growth involves a sequence of bacterial and fungal attacks in which each attack renders the paint film susceptible to the metabolic processes of the next attacking organism. For effective mildew inhibition, a mildewcide must be active against a significant number of microbial species, bacterial and fungal, and especially effective against those species which cause initial damage to the paint film.

The addition of currently known mildewcidal agents such as 2-n-octyl-4-isothiazolin-3-one ("SKANE M-8") or N-pentachlorophenylethylenediamine to paint formulations provides excellent initial antimicrobial response in various paint films. However, these agents generally provide only temporary mildew inhibitions, since they are susceptible to chemical change and deactivation while still in the paint formulation, and to further deactivation in the paint film. Under outdoor environmental exposures these agents may also be subject to leaching from the paint films. A need clearly exists to develop a means of providing extended protection of paint films against mildew attack.

One method, proposed by Pittman, *J. of Coatings Technology;* 48(617), 31–7 (1976), of extending the effective life of a mildewcidal agent involves the chemical anchoring of the mildewcidal agent to a component in the paint film, e.g., the latex polymer, thus reducing the tendency of leaching of the agent from the paint film and effectively increasing the useful lifetime of the mildewcidal agent.

Lutz et al., *Organic Coatings and Plastics Chemistry,* Vol. 38, 195–201 (1976), describes the use of methyltrimethoxysilane to reinforce various organic formulations. Dried films of such reinforced latexes gave improved solvent resistance.

Other references forming part of the background of the present invention are: U.S. Pat. No. 3,253,009, which discloses silanes and siloxanes containing a moiety (RO)Si wherein R is a halogen-substituted aryl group; U.S. Pat. No. 3,542,786, which discloses compounds such as

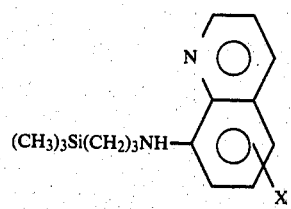

wherein X is chlorine or fluorine; U.S. Pat. No. 3,692,798 which discloses compounds of the formula

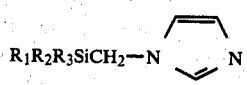

wherein each of $R_1$, $R_2$, and $R_3$ is lower alkyl or phenyl; U.S. Pat. No. 3,719,679, which discloses N-methyl- and N,N-dimethyl-3-[tris(trimethylsilyloxy)silyl]propanamine; U.S. Pat. No. 3,860,709, which discloses compounds such as that of the formula $(CH_3O)_3Si(CH_2)_3NH(CH_2)_2NH_2$ and other simpler and more complex organosilicon amines and their salts; British Pat. No. 1,386,876, which discloses organosilicon quaternary ammonium compounds; Canadian Pat. No. 1,010,782, which discloses filled polymeric matrices containing solid fillers which fillers have coated on their surfaces organosilicon quaternary ammonium compounds; West German Offenlegungsschrift No. 1,806,758, which describes various phenolic and quarternary ammonium derivatives of phenyltrichlorosilane; and West German Offenlegungsschrift No. 2,632,417, which describes various organosilicon quaternary ammonium halides.

None of the above-noted references discloses or suggests the novel class of silane derivatives upon which the present invention is founded.

SUMMARY OF THE INVENTION

The present invention comprises novel mildewcidal compounds of the formula

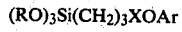

wherein R is alkyl of up to eight carbon atoms, X is —NHC(O)— or —S(CH$_2$)$_2$C(O)—, and Ar is selected from the group consisting of

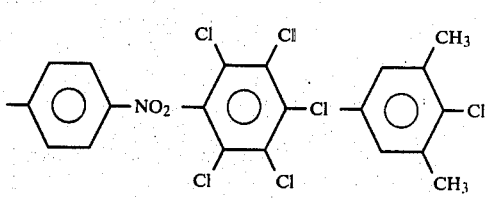

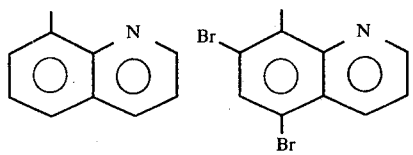

Another aspect of the present invention is the use of such novel mildewcidal compounds in latex paints.

The present invention also contemplates the extension of mildew protection lifetime by the immobilization of the mildewcidal agents on the surface of inorganic fillers, e.g., silicas, such as are incorporated into most paints. Fillers so treated are a still further aspect of the present invention. The treated filler becomes the carrier for incorporation of the mildewcidal agent into a paint film. This method is an economically and technologically interesting means of achieving extended mildew inhibition. Utilization of mildewcidal silanes avoids the difficult problems encountered in the preparation of latex polymers containing chemically combined mildewcidal agents. This approach also provides considerable latitude in the use of mixtures of agents and varying concentrations to achieve synergistic and optimum effects.

DESCRIPTION OF THE PREFERRED EMBODIMENTS

The novel mildewcidal compounds of the present invention have the formula

(RO)$_3$Si(CH$_2$)$_3$XOAr wherein R is alkyl of up to eight carbon atoms, and is preferably methyl or ethyl, X is —S(CH$_2$)$_2$C(O)— or is —NHC(O)—, and Ar is selected from the radicals

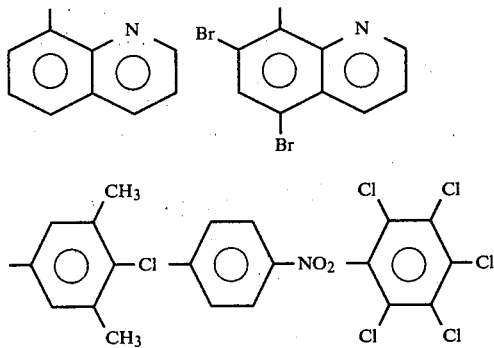

Specific examples of the compounds of the present invention include:

(EtO)$_3$Si(CH$_2$)$_3$NC(O)O—⟨O⟩—NO$_2$

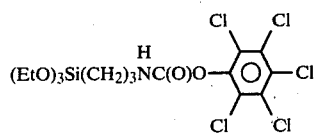

(EtO)$_3$Si(CH$_2$)$_3$NC(O)O—⟨O⟩—Cl (with Cl substituents)

(MeO)$_3$Si(CH$_2$)$_3$NC(O)O—⟨O⟩—Br (with Br substituent)

(EtO)$_3$Si(CH$_2$)$_3$NC(O)O—⟨O⟩ (quinoline)

(MeO)$_3$Si(CH$_2$)$_3$S(CH$_2$)$_2$C(O)O—⟨O⟩—NO$_2$ (MeO)$_3$Si(CH$_2$)$_3$S(CH$_2$)$_2$C(O)O—⟨O⟩—Cl (with Cl substituents)

(MeO)$_3$Si(CH$_2$)$_3$S(CH$_2$)$_2$C(O)O—⟨O⟩ (quinoline)

(MeO)$_3$Si(CH$_2$)$_3$S(CH$_2$)$_2$C(O)O—⟨O⟩—Cl (with CH$_3$ substituents)

The compounds of the present invention can be utilized both individually and in combination with each other and/or with other mildewcidal silanes such as, e.g., that disclosed in above-mentioned Ser. No. 192,603 to provide a long-lasting mildewcidal effect in latex paints. A compound, or a combination of two or more compounds, can be incorporated directly into a latex paint mixture, or it or they can be coated onto a silica filler which is then incorporated into a latex paint mixture.

The aryl carbamate embodiments of the present invention can be prepared by the triethylamine-catalyzed reaction of appropriate phenolic-functional aryl precursors with gamma-isocyanatopropyltrialkoxysilanes as follows:

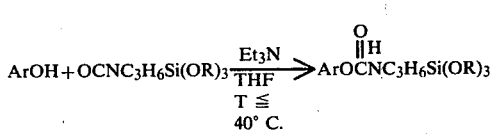

$$\text{ArOH} + \text{OCNC}_3\text{H}_6\text{Si(OR)}_3 \xrightarrow[\text{THF}]{\text{Et}_3\text{N}} \text{ArOCNC}_3\text{H}_6\text{Si(OR)}_3$$
T ≦ 40° C.

The reactions are run at moderate temperatures to avoid the following thermal degradation of the carbamate product.

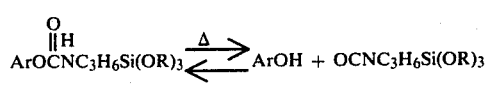

The yields of these reactions were determined by infrared spectroscopy to be greater than 98%.

Illustrative specific examples follow:

EXAMPLE I

Illustrates the Preparation of N-(gamma-Triethoxysilylpropyl)-O-pentachlorophenyl Carbamate 28.0 Parts of gamma-isocyanatopropyltriethoxysilane, 25.0 parts of pentachlorophenol, 0.5 parts of triethylamine and 75.0 parts of diethyl ether were mixed in tightly stopped 200 ml round bottom flask for 24 hours. The flask contents were then evaporated under reduced pressure, 20 mmHg, and 42° C. to yield a white solid. Infrared spectroscopy showed that N-(gamma-triethoxysilylpropyl)-O-pentachlorophenyl carbamate was prepared in 91.6% purity.

EXAMPLE II

Substituting p-nitrophenol for the pentachlorophenol in Example I leads to the production of N-(gamma-triethoxysilylpropyl)-O-p-nitrophenyl carbamate.

EXAMPLE III

Substituting 8-hydroxyquinoline for the pentachlorophenol in Example I leads to the production of N-(gamma-triethoxysilylpropyl)-O-8-quinolyl carbamate.

EXAMPLE IV

Substituting gamma-isocyanatopropyltrimethoxysilane for the gamma-isocyanatopropyltriethoxysilane and 5,7-dibromo-8-hydroxyquinoline for the pentachlorophenol in Example I leads to the production of N-(gamma-trimethoxysilylpropyl)-O-5,7-dibromo-8-quinolyl carbamate.

The ester embodiments of the present invention can be prepared by a sequence of two reactions. After the preparation of the acrylate esters of the appropriate phenolic-functional aryl precursors, gamma-mercaptopropyltrialkoxysilane is reacted via a radical addition as shown:

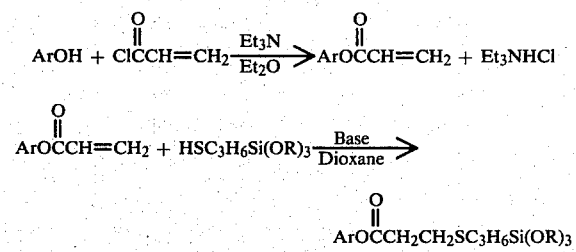

Illustrative specific examples follow:

EXAMPLE V

Illustrates the Preparation of 8-(3-S-7 trimethoxysilyl heptanoyl)quinoline 25.0 Parts of 8-hydroxyquinoline, 30.4 parts of triethylamine, and 200 parts of diethylether were added to a 500 ml three neck, round bottom flask, equipped with a thermometer, dropping funnel with a nitrogen bypass, and mechanical stirrer. The flask contents were cooled to 0° C. using an external ice bath at which point 23.8 parts of acryloyl chloride were added dropwise. The flask contents were maintained below −20° C. by cooling with an ice bath. After addition was complete, the flask contents were stirred at 25°–30° C. for three hours at which point the contents were poured into a separatory funnel and extracted with 200 ml water followed by two extractions with 10% potassium carbonate and a final extraction with saturated potassium bromide. The ethereal layer was then dried over anhydrous magnesium sulfate. The dried ethereal layer was then stripped under reduced pressure over a 35° C. water bath. 23.0 parts of 8-hydroxyquinoline acrylate was made as shown to be of 98% purity by gas chromatography and infra-red spectroscopy.

7.0 parts of 8-hydroxyquinoline acrylate, 7.6 parts of γ-mercaptopropyltrimethoxysilane, 0.05 parts of sodium methoxide and 50.0 parts of dioxane were charged to a 100 ml, round bottom flask equipped with a magnetic stirrer and water condenser with a nitrogen bypass. The flask contents were then cooled to 0° C. with an external ice bath at which point 1.0 part of piperidine was added. The flask contents were allowed to warm to 20°–25° C. and were subsequently stirred at 25° C. for 72 hours. The flask contents were then stripped under reduced pressure (0.8 mmHg) to 110° C. on a kugelrohr distillation apparatus. The crude product was analyzed by infra-red and nuclear magnetic resonance spectroscopy.

EXAMPLE VI

Substituting p-nitrophenol for the 8-hydroxylquinoline in Example V leads to the preparation of 4-(3-S-7-trimethoxysilyl-heptanoyl)nitrobenzene.

EXAMPLE VII

Substituting pentachlorophenol for the 8-hydroxyquinoline in Example V leads to the preparation of 6-(3-S-7-trimethoxysilyl-heptanoyl) pentachlorobenzene.

EXAMPLE VIII

Substituting 4-chloro-3,4-dimethylphenol for the 8-hydroxyquinoline of Example V leads to the preparation of 2,6-dimethyl-4-(3-S-7-trimethoxysilyl-heptanoyl)chlorobenzene.

BIOLOGICAL TESTING RESULTS

A. Agar Screening Tests: Compounds

This is a general preliminary screening of representative compounds of the present invention for their potential mildewcidal activity.

The compounds were dispersed in an agar suspension at a concentration of 500 parts per million (ppm) and subsequently inoculated with six fungal and six bacterial specimens. The fungal and bacterial species were representative species previously found to be present at various stages of mildew growth. A mildewcidal candidate has an excellent chance of providing effective mildew protection in a latex paint film, under normal weathering conditions, if it inhibits the growth of all twelve microorganisms at 500 ppm or lower in this test.

The agar to be used, CZAPEK DOX nutrient agar for fungal and bacterial growth testing, was sterilized and subsequently cooled to 55° C. At this time, the desired agar suspension was then poured into a sterilized petri-dish and allowed to harden overnight. The resulting agar plates were then inoculated with the desired bacterial suspension or fungal spore suspension (see listing below) with a multiple point inoculator. (All bacterial and fungal spore suspensions were fresh and of standardized activity.) The inoculated agar plate was allowed to air dry in a lammelar flow hood and subsequently incubated at 30° C. for 7 days. Comparison of bacterial or fungal growth was compared to appropriate control preparations.

Suspensions of the following bacteria were used:

(1) *Bacillus megaterium*
(2) *Enterobacter aerogenes*
(3) *Escherichia coli*
(4) *Proteus vulgaris*
(5) *Pseudomonas aeruginosa*
(6) *Pseudomonas putidas*

Suspensions of the following fungi were used:

(1) *Aspergillus niger*
(2) *Aureobasidium pullulons*
(3) *Fusarium moniliforme*
(4) *Penicillium citrinum*
(5) *Stemphylium sp.*
(6) *Trichoderma viride*

The biocidal activity was evaluated on a scale of from 0 to 6, where 0 indicates ineffectiveness and 6 indicates total inhibition. The results are reported in Table I.

TABLE I

| Compound of Example No. | Activity | |
|---|---|---|
| | Fungicidal | Bactericidal |
| I | 6 | 4 |
| II | 5 | 6 |
| III | 6 | 5 |
| IV | 6 | 5 |
| V | 6 | 5 |
| VI | 6 | 5 |
| VII | 6 | 3 |
| VIII | 6 | 2 |

B. Agar Screening Tests: Treated Fillers

This is an agar screening test which was used to evaluate the antimicrobial activity of various silane treated silica compounds. This test is performed by dispersing a mildewcidal silane treated silica in an agar suspension and subsequent inoculation with the same six fungal and six bacterial species used in the agar screening tests of compounds reported above.

In a typical example of filler treatment, 2718.0 parts of amorphous silica filler (IMSIL A-25, Illinois Minerals, Inc.) was charged into a Patterson-Kelly Twin Shell blender equipped with a high speed intensifier bar and a dropping funnel attached to the Twin Shell blender. The silane solution was then added to the tumbling silica filler with the high speed intensifier bar on. After the silane addition was complete, the filler was tumbled with the high speed intensifier bar on for an additional 15 minutes at which time the wet filler mixture was charged to a large pan and dried for 20 minutes at 40° C. The dried silica was then stored in a tightly capped glass jar until used.

The agar to be used, CZAPEK DOX nutrient agar for fungal and bacterial growth testing, was sterilized and subsequently cooled to 55° C. At this time, the desired agar suspension was dispensed into a 25 ml polypropylene cup. The particular silane treated silica filler to be evaluated was then hand stirred into the agar suspension and the resulting silica/agar suspension was poured into a sterile petri-dish and allowed to harden overnight. The resulting agar plates were then inoculated with the desired bacterial suspension or fungal spore suspension (same as those listed in above) with a multiple point inoculator. (All bacterial and fungal spore suspensions were fresh and of standardized activity.) The inoculated agar plate was allowed to air dry in a lammelar flow hood and subsequently incubated at 30° C. for 7 days. Comparison of bacterial or fungal growth was compared to appropriate control preparations.

The biocidal activity was evaluated on a scale of from 0 to 6, where 0 indicates ineffectiveness and 6 indicates total inhibition. The results are reported in Table II.

TABLE II

| Compound of Example No. | Weight % of Compound on Silica | Activity | |
|---|---|---|---|
| | | Fungicidal | Bactericidal |
| Control (Silica, No Silane Compound) | 0.0 | 0 | 0 |
| I | 1.2 | 6 | 1 |
| II | 1.2 | 6 | 5 |
| I/II* | 1.2 | 6 | 6 |
| V | 1.2 | 6 | 5 |
| VI | 1.2 | 6 | 6 |
| VII | 1.2 | 6 | 3 |

*1:1 weight mixture

C. Paint Tests

The particular agar screening test used for this evaluation also gives a preliminary indication of the leach resistant properties of the mildewcidal silane in the paint film. This is seen by comparing the zone of inhibition of the non-silylated mildewcide with its silylated analog. The zone of inhibition is due to the mildewcide migration from the paint film into the agar suspension. The information shown in Table III shows that although migration of the pentachlorophenol and the 8-hydroxyquinoline produced zones of inhibition, the respective silylated derivatives showed none. It should be noted that the smaller zone of inhibition of the pentachlorophenol is due to the more hydrophobic nature of the compound.

The test paint is prepared in the following two steps:

Step 1: 136.4 parts of deionized water, 20.0 parts of ethylene glycol and 1.5 parts of a hydroxyethyl cellulose thickener were charged into a 1 liter stainless steel beaker and stirred at 625 rpm with a Cowles mixer until complete dissolution was observed. At this point, the following components were added by the indicated order of addition.

| Addition Order | Component | Parts |
|---|---|---|
| 1 | Acid functional Acrylic Dispersing Agent (Tamol 850) | 16.0 |
| 2 | Potassium Tripolyphosphate | 1.8 |
| 3 | Defoamer (Nopco NXZ) | 1.2 |
| 4 | Wetting Agent (Triton CF-10) | 2.8 |
| 5 | Titanium Dioxide Pigment (Ti-Pure R-900) | 244.0 |
| 6 | IMSIL A-25 Filler (treated as in Section B above) | 244.0 |

The total component mixture was stirred for 15 minutes after the above addition was completed and then was allowed to cool to room temperature.

Step 2: The following ingredients, in the indicated order of addition, were added to the component mixture from Step 1 above and stirred with a "lightning mixer":

| Addition Order | Component | Parts |
|---|---|---|
| 1 | A 53% Acrylic latex (UCAR Latex 508) | 372.0 |
| 2 | Anaerobic Preservative (Proxcel CRL)* | 1.0 |
| 3 | Non-ionic Nonylphenol Ethoxylate surfactant (TERGITOL NPX) | 2.0 |
| 4 | Alkyd Resin Adhesive Promoter (Aroplaz 1271 Alkyd) | 46.0 |
| 5 | Cobalt Naphthenate (12% "NuxTra" Cobalt Drier) | 0.8 |
| 6 | Zirconium Naphthenate (12% "NuxTra" Zirconium Drier) | 0.8 |
| 7 | Isobutyl Isobutyrate (Texanol) | 10.8 |
| 8 | 2% Water Solution of Hydroxyethyl Cellulose Thickener (CELLOSIZE HEC QP-4400) | 184.0 |
| 9 | Defoamer (Nopco NXZ) | 2.6 |

*An "in-can" stabilizer

The above mixture was stirred for 10 minutes after the addition was complete. At this point, the total paint mixture was adjusted to pH 9.0 using concentrated ammonium hydroxide. The viscosity of the various test paint formulations were typically 95–105 Kreb units.

A thin film of the desired paint composition was brush-painted onto a one-inch square ceramic tile block. The painted block was allowed to dry at room temperature for 4 days in a lammelar flow hood. The painted block was then placed in the center of a sterilized petri-dish which was subsequently filled with sterilized CZAPEK DOX agar at 55° C. to the top edge of the block. The agar was then hand inoculated with three different fungal spore suspensions. A second agar/painted ceramic tile block was prepared in the same manner and hand inoculated with three different fungal spore suspensions. (The fungi used are listed above.) In this manner six different fungi were evaluated. The inoculated specimens were incubated at 30° C. for two weeks at which time growth comparisons with appropriate controls was performed.

TABLE III

DEMONSTRATION OF ANTIMICROBIAL ACTIVITY OF VARIOUS PAINT FILMS INCORPORATING MILDEWCIDAL SILANES

| Biocide | Biocide Concentration (%)[1] | Fungal Inhibition | Zone of Inhibition[2] |
|---|---|---|---|
| Control | 0.0 | None | — |
| 8-Hydroxyquinoline | 0.77 | Complete | Total |
| Compound of Example V | 0.77 | Complete | None |
| Pentachlorophenol | 6.4 | Complete | Small |
| Compound of Example I | 6.4 | Complete | None |

[1]Represents the concentration of mildewcide in the dried paint film.
[2]The zone of inhibition is a measure of biocide migration out of the paint film into the agar mixture.

D. Long Term Paint Exposure Tests

Paints were prepared as described above in Section C but incorporating the mildewcidal agents indicated in Tables IV and V. The paints were applied to standard white pine test panels which are conventionally used for prolonged exterior exposure studies of paint films. The painted panels were then subjected to prolonged exposure studies at testing facilities (1) in Largo, Fla. and (2) in South Chrleston, W. Va. The exposure conditions at the Largo Test Facility are particularly severe with respect to mildew growth. The results obtained here approximate a "worst case" situation since even many excellent mildewcidal compounds may fail after relatively short exposure trials. The testing facility at South Charleston is considerably less severe and provides a more realistic test with respect to the severity of exposure conditions. In addition to mildew protection, the South Charleston facility also evaluated the discoloration of the painted panels due to weathering. The results are reported in Tables IV and V.

TABLE IV

MILDEWCIDAL SILANE EXTERIOR EXPOSURE RESULTS OBTAINED AT THE LARGO, FLORIDA TESTING FACILITY

| Mildewcide | (Conc.)[2] | Monthly Mildew Defacement Rating[3] | | | | |
|---|---|---|---|---|---|---|
| | | 2 | 3 | 4 | 5 | 6 |
| None | (0.0) | 4 | 2 | 2 | 0 | 0 |
| Skane M-8[1] | (0.05) | 10 | 6 | 2 | 2 | 2 |
| Compound of Example I | (0.05) | 4 | 2 | 2 | 2 | 0 |
| Compound of Example I | (0.23) | 6 | 3 | 3 | 2 | 2 |
| Compound of Example I | (1.9) | 8 | 2 | 2 | 3 | 2 |
| Compound of Example I[1] | (1.9) | 8 | 6 | 6 | 4 | 4 |
| Compound of Example II | (0.06) | 6 | 3 | 2 | 2 | 0 |
| Compound of Example II | (0.23) | 8 | 6 | 2 | 2 | 2 |

[1]In these examples, the mildewcidal silane was added directly to the pigment grind.
[2]Mildew concentration is based on the total weight of the paint blend. The mildewcidal silanes were typically added to paint via silane treated IMSIL silica filler.
[3]Paint ratings 1 = worst, 10 = best.

TABLE V

MILDEWCIDAL SILANE EXTERIOR EXPOSURE RESULTS OBTAINED AT THE SOUTH CHARLESTON TESTING FACILITY

| Mildewcidal | (Conc.)[2] | Mildew Defacement[3] | | Discoloring[3] | |
|---|---|---|---|---|---|
| | | 6 months | 1 year | 6 Months | 1 Year |
| None | (0.0) | 3 | 2 | 4 | 4 |
| Skane M-8[1] | (0.05) | 6 | 4 | 5 | 5 |
| Compound of Example I | (0.05) | 4 | 8 | 6 | 6 |
| Compound of Example I | (0.23) | 5 | 7 | 5 | 4 |
| Compound of Example I | (1.9) | 7 | 7 | 5 | 4 |
| Compound of Example I[1] | (1.9) | 6 | 3 | 5 | 4 |
| Compound of Example II | (0.06) | 3 | 5 | 5 | 4 |

TABLE V-continued

MILDEWCIDAL SILANE EXTERIOR EXPOSURE RESULTS OBTAINED AT THE SOUTH CHARLESTON TESTING FACILITY

| Mildewcidal | (Conc.)[2] | Mildew Defacement[3] | | Discoloring[3] | |
|---|---|---|---|---|---|
| | | 6 months | 1 year | 6 Months | 1 Year |
| Compound of Example II | (0.23) | 6 | 6 | 4 | 3 |

[1] In these examples, the mildewcidal silane was added directly to the pigment grind.
[2] Mildewcide concentration based on the total weight of the paint blend. The mildewcidal silanes were typically added to the paint via silane treated IMSIL silica filler. The non-silylated mildewcide was typically added directly to the pigment grind.
[3] Paint ratings are 1 = worst, 10 = best.

What is claimed is:

1. A compound of the formula $$(RO)_3Si(CH_2)_3XOAr$$

wherein R is alkyl of up to eight carbon atoms, X is —NHC(O)— or —S(CH$_2$)$_2$C(O)—, and Ar is selected from the group consisting of p-nitrophenyl, pentachlorophenyl, 4-chloro- 3,5-dimethylphenyl, 8-quinolyl, and 5,7-dibromo-8-quinolyl.

2. A compound of the formula $$(RO)_3Si(CH_2)_3XOZ$$

wherein R is an alkyl group of up to eight carbon atoms, X is —NCH(O)— or —S(CH$_2$)$_2$C(O)—, and Z is 8-quinolyl or 5,7-dibromo-8-quinolyl.

3. A compound according to claim 1 which has the formula (C$_2$H$_5$O)$_3$Si(CH$_2$)$_3$NHC(O)O—[pentachlorophenyl]

4. A compound according to claim 1 which has the formula (C$_2$H$_5$O)$_3$Si(CH$_2$)$_3$NHC(O)O—[phenyl]—NO$_2$ 5. A compound according to claim 2 which has the formula (C$_2$H$_5$O)$_3$Si(CH$_2$)$_3$NHC(O)O—[8-quinolyl]

6. A compound according to claim 2 which has the formula (C$_2$H$_5$O)$_3$Si(CH$_2$)$_3$NHC(O)O—[5,7-dibromo-8-quinolyl]

7. A compound according to claim 2 which has the formula (CH$_3$O)$_3$Si(CH$_2$)$_3$S(CH$_2$)$_2$C(O)O—[8-quinolyl]

8. A compound according to claim 1 which has the formula (CH$_3$O)$_3$Si(CH$_2$)$_3$S(CH$_2$)$_2$C(O)O—[phenyl]—NO$_2$ 9. A compound according to claim 1 which has the formula (CH$_3$O)$_3$Si(CH$_2$)$_3$S(CH$_2$)$_2$C(O)O—[pentachlorophenyl]

10. A compound according to claim 1 which has the formula (CH$_3$O)Si(CH$_2$)$_3$S(CH$_2$)$_2$C(O)O—[4-chloro-3,5-dimethylphenyl]

11. A compound according to claim 1 in combination with a different compound according to claim 1.

* * * * *